United States Patent [19]

Price

[11] Patent Number: 4,605,648

[45] Date of Patent: Aug. 12, 1986

[54] TREATMENT OF HERPES SIMPLEX VIRUSES

[76] Inventor: E. Pendleton Price, P.O. Box 102, Kitty Hawk, N.C. 27949

[21] Appl. No.: 766,100

[22] Filed: Aug. 15, 1985

[51] Int. Cl.$^4$ .............................................. A61K 31/56
[52] U.S. Cl. .................................................. 514/180
[58] Field of Search ........................................ 514/180

[56] References Cited

U.S. PATENT DOCUMENTS 2,838,491  6/1958  Herr et al. ........................ 260/239.5
3,322,627  5/1967  Shen ..................................... 514/274

OTHER PUBLICATIONS

PDR, 35th Ed., 1981, p. 1824.

*Primary Examiner*—Jerome D. Goldberg
*Attorney, Agent, or Firm*—Bell, Seltzer, Park & Gibson

[57] ABSTRACT

A method of suppressing the outbreaks of Herpes Simplex virus lesions and related symptoms in humans by administering to an individual who has experienced Herpes Simplex virus outbreaks a therapeutically effective dosage of an androgenic flurosteroid.

4 Claims, No Drawings

TREATMENT OF HERPES SIMPLEX VIRUSES

FIELD OF THE INVENTION

This invention relates generally to the treatment of herpes viruses and more particularly concerns the treatment of Herpes Simplex II viruses and the suppression of the characteristic lesions and other symptoms of the disease.

BACKGROUND OF THE INVENTION

Herpes Simplex is the full name of a virus best known for causing cold sores, fever blisters and the genital infections that have become widespread in the past decade. The herpes simplex viruses belong to a family of four DNA viruses that are collectively known as herpes-viruses and include those viruses which cause chicken pox, shingles, mononucleosis and encephalitis. The herpes viruses are characterized by two distinct features: they effect mainly human beings and their infection is never completely eradicated by the body's immune system. Instead, the virus lies dormant in the body and tends to become reactivated many times or many years after the initial infection, accompanied by their characteristic symptoms.

The symptoms of the herpes virus have been described for thousands of years, but recent trends show a significant rise in the number of cases. Current estimates are that between 5 and 20 million Americans have herpes and that between 300,000 and 500,000 new cases occur each year.

Within the last several decades, it has been discovered that the Herpes Simplex virus occurs in two characteristic forms, type I and type II. Generally, type I has been recognized as causing the characteristic cold sore while type II has caused the genital symptoms to be discussed herein. Currently, both types of Herpes Simplex can be found in both locations in various patients, probably resulting from various forms of personal contact. The usual symptoms of the Herpes Simplex II genital infection include painful blisters or ulcers, itching or burning, swollen lymph glands, urethritis, proctitis, fever, muscle aches and a vague feeling of being unwell.

Treatment of Herpes Simplex II is complicated by its viral character and by its characteristic residence in the nervous system rather than the blood stream. Shortly after entering the human body, the virus tends to move to the nervous system near the base of the spinal cord where it may live indefinitely. Consequently, antibodies—substances which the body normally attempts to produce in response to certain invading harmful substances—circulating in the bloodstream cannot reach the herpes virus to attack or destroy it.

The most common and troublesome characteristic of the Herpes Simplex II virus is its repeated eruption into active phases following some outside stimulus such as physical or emotional stress, the female menstrual period, sexual activity, exposure to heat or cold, use of alcohol, sunburn, physical exertion, or other similar conditions. During these active phases of the disease, the physical outbreaks cause the virus to "shed" so that close contact with another person can result in transmission of the disease. Some evidence also exists that the Herpes Simplex II virus causes cancer and if left untreated, the presence of the virus can cause the illness or death of a newborn child born during one of the outbreaks of an infected mother.

Several treatments have been developed for those affected by the disease. One recently approved treatment is the drug acyclovir marketed under the trade name ZOVIRAX. As an ointment, this medication allegedly reduces the pain and duration of outbreaks and may give some relief from the flu-like symptoms that often accompany the attacks. Nevertheless, acyclovir apparently is only useful during an outbreak and patients using the ointment must begin to use it as soon as the initial tingling symptoms appear prior to the characteristic outbreak of the lesions. Additionally, ZOVIRAX is expected to be expensive with the typical dosage for six months costing several hundred dollars.

Another, more typical approach for attacking the herpes virus is the use of a vaccine. Vaccines are typically manufactured from intact viruses which are injected into the human body in a very mild form. Ideally, the body responds to the weak form of the virus by producing specific antibodies against it. These antibodies are then sufficient to prevent outbreaks of stronger versions of the viruses with which the vaccinated person may later come in contact.

Nevertheless, vaccines normally represent preventative medicines rather than cures. Additionally, vaccines carry the risk that they may cause an occasional outbreak of the disease they are intended to prevent. For example, a few cases of polio result each year from the use of polio vaccines. Furthermore, because of the cancer risk presented by the herpes virus and the particularly serious complications and side effects of the disease, the risks of vaccination are currently considered somewhat greater than they are in the treatment of some other diseases.

Other attempts at attacking the virus have included the manufacture of subunit vaccines, i.e. vaccines made from the antigen portions of a virus. Antigens are the substances which stimulate the body to produce the appropriate antibody to combat the virus. Antigens do not contain genetic material and thus theoretically cannot cause the disease. Currently, however, the use of subunit vaccines is still in an experimental stage and some scientific critics contend that even subunit vaccines still carry the same risk of infection as normal vaccines.

Consequently, work is continuing in developing totally synthetic vaccines from genetically engineered versions of one or more of the herpes antigens, while other researchers are aiming at altering the genetic makeup of live herpes viruses so that they can safely be used to develop vaccines having a strong immune response in human beings.

There thus currently exists no acceptable vaccines for treating the herpes virus and no other medication which can be used other than to moderate the effects of the herpes outbreaks and their characteristic lesions.

It is thus an object of the present invention to provide a treatment for herpes viruses and their characteristic outbreaks and symptoms which does not carry the risks associated with vaccination, which can be used in more than topical application and which can suppress and prevent outbreaks of the characteristic symptoms of the disease instead of just moderating them once they appear.

It is a further object of the present invention to provide a treatment of the outbreaks of Herpes Simplex II viruses which suppresses the outbreak of the lesions and characteristic of this strain of the virus which consequently suppresses the shedding of active Herpes Simplex II viruses which can be transmitted by an infected party.

DETAILED DESCRIPTION OF THE INVENTION

The invention comprises a method of treating herpes viruses and their characteristic and related symptoms by administering to an individual who suffers from one of the herpes virus infections a therapeutically effective dosage of an androgenic steroid. As known to those familiar with the art, steroids are a class of chemical compounds which are characterized by their particular chemical structure. Steroids always include three six-membered rings and a fourth five-member ring which are generally aliphatic and each of which rings is fused to the adjacent ring or rings at two carbon positions in either cis or trans relationships. Some human steroids include sex hormones and adrenal cortical hormones (cortisone), cardiac glycosides and bile acids. Because of their biological importance and the particular complexity of their chemistry, the study of steroids has historically been, and continues to be, an active area of organic chemical research.

An androgenic steroid is one of the class of steroid hormones which play a major role in the development and maintenance of masculine secondary sexual characteristics. Androgens or androgenic steroids exhibit the characteristic ring structure of all steroids and additionally are characterized by particular substitutionary functional groups at specific locations along the ring structure.

In the preferred embodiment of the invention, the androgenic steroids of choice are androgenic fluorosteroids and the specific steroid fluoxymesterone has been found to be particularly effective. Fluoxymesterone is marketed under the trade name HALOTESTIN by the Upjohn Company and under the trade name ANDROID-F by the Brown Pharmaceutical Company, Inc. One formal designation for fluoxymesterone is 9-fluoro-11,17-dihydroxy-17-methylandrost-4-en-3-one. As used herein, the more common name fluoxymesterone will be used to refer to this compound.

In a broad sense, the invention comprises treating any one of the four types of herpes viruses and their characteristic symptoms with steroid and particularly with the androgenic fluorosteroid fluoxymesterone.

In more specific embodiments, the method comprises suppressing the outbreaks of herpes simplex virus lesions and their related symptoms in humans by administering to an individual who has experienced herpes simplex virus outbreaks a therapeutically effective dose of a androgenic steroid.

In the preferred embodiment, the invention comprises a method of suppressing the outbreaks of Herpes Simplex II viruses and related symptoms in humans by orally administering to an individual who has experienced Herpes Simplex II virus outbreaks between about 1 and 40 milligrams per day of fluoxymesterone, with a preferred amount being between about 10 and 20 milligrams per day of fluoxymesterone.

The following clinical example exhibits the successful use of the invention in combating and suppressing the outbreaks of Herpes Simplex II virus lesions and their related symptoms.

EXAMPLE

The subject was an adult female who contracted Herpes Simplex II through sexual contact with an infected partner. The virus first manifested itself as a characteristic rash on the subject's left buttock. After examination by several specialists, the subject was diagnosed as having Herpes Simplex II. The characteristic symptoms, including lesions, appeared on a generally monthly basis after any of the following events: sexual intercourse, menstrual period, ingestion of alcohol, sunburn, exposure to extreme heat including hot baths or whirlpools, exposure to cold, particularly stressful mental situations, nervous tension or physical exertion. The outbreaks experienced by the subject would last for at least two weeks and often would last longer.

Some eight years after first contracting the virus and experiencing the monthly outbreak of symptoms as described previously, the subject developed a second, unrelated blood disorder. Approximately two months after diagnosis of this second condition, fluoxymesterone was prescribed to the subject for treatment of the blood disorder. Since beginning a prescription of 20 milligrams per day of fluoxymesterone, an 11 month time period to date, the subject has not experienced any outbreaks of Herpes Simplex II virus symptoms, including the characteristic lesions. The subject took no other medications during this time period.

During this course of treatment, and since beginning to receive the 20 milligram per day dosage of fluoxymesterone, the subject has been exposed to all of the above listed situations which historically have brought on the outbreaks of the virus lesions in this subject and which characteristically bring the symptoms on in most other subjects who suffer from the Herpes Simplex II virus infections.

Although fluoxymesterone is an available prescription drug, there presently exists no suggestion that it would have antiviral activity on any of the herpes viruses nor on the Herpes Simplex II virus in particular. Fluoxymesterone is generally prescribed to male patients for eunuchoidism, eunuchism, climacteric symptoms, panhypopituitarism, impotence and delayed puberty. In females, fluoxymesterone has been prescribed for prevention of postpartum breast pain and engorgement as well as palliation of androgen responsive, advancing inoperable mammary cancer.

In other applications, fluoxymesterone has been used as part of fluid protein assays, as an oral male contraceptive composition, as an ingredient in an ocular therapeutic system and as part of various methods of therapeutic delivery of indicated medications for particular conditions.

The foregoing embodiments are considered to be illustrative, rather than restrictive of the invention, and those modifications which come within the meaning and range of equivalence of the claims are to be included therein.

That which is claimed is:

1. A method for treating herpes simplex virus infections which comprises orally administering to a human in need of said treatment an antiviral effective amount of fluoxymesterone.

2. A method according to claim 1 wherein said amount comprises between about 1 and 40 milligrams per day.

3. A method according to claim 1 wherein said amount comprises between about 5 and 30 milligrams per day.

4. A method according to claim 1 wherein said amount comprises between about 10 and 20 milligrams per day.

* * * * *